US011384312B2

(12) United States Patent
Leyssene et al.

(10) Patent No.: US 11,384,312 B2
(45) Date of Patent: Jul. 12, 2022

(54) FRAGRANCE COMPOSITIONS AND METHODS OF USE THEREOF

(71) Applicant: TAKASAGO INTERNATIONAL CORPORATION, Tokyo (JP)

(72) Inventors: Bruno Leyssene, Rockleigh, NJ (US); Louis J. Lombardo, Washingtonville, NY (US); Raphael K. L. Kang, Leonia, NJ (US); Alba T. Cilia, River Edge, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 58 days.

(21) Appl. No.: 16/311,031

(22) PCT Filed: Jun. 29, 2017

(86) PCT No.: PCT/US2017/040070
§ 371 (c)(1),
(2) Date: Dec. 18, 2018

(87) PCT Pub. No.: WO2018/005844
PCT Pub. Date: Jan. 4, 2018

(65) Prior Publication Data
US 2019/0358137 A1 Nov. 28, 2019

Related U.S. Application Data

(60) Provisional application No. 62/356,516, filed on Jun. 29, 2016.

(51) Int. Cl.
| A61K 8/34 | (2006.01) |
| A61K 8/35 | (2006.01) |
| A61K 8/37 | (2006.01) |
| A61K 8/49 | (2006.01) |
| A61Q 13/00 | (2006.01) |
| C11B 9/00 | (2006.01) |
| A61P 25/20 | (2006.01) |
| A61K 31/015 | (2006.01) |
| A61K 31/045 | (2006.01) |
| A61K 31/122 | (2006.01) |
| A61K 31/215 | (2006.01) |
| A61Q 15/00 | (2006.01) |

(52) U.S. Cl.
CPC .............. *C11B 9/0034* (2013.01); *A61K 8/34* (2013.01); *A61K 8/35* (2013.01); *A61K 8/37* (2013.01); *A61K 8/498* (2013.01); *A61K 31/015* (2013.01); *A61K 31/045* (2013.01); *A61K 31/122* (2013.01); *A61K 31/215* (2013.01); *A61P 25/20* (2018.01); *A61Q 13/00* (2013.01); *A61Q 15/00* (2013.01)

(58) Field of Classification Search
None
See application file for complete search history.

(56) References Cited

U.S. PATENT DOCUMENTS

| 1,994,932 A | 3/1935 | Lucien |
| 2,597,195 A | 5/1952 | Smith |
| 2,802,695 A | 8/1957 | Johnson |
| 2,804,291 A | 8/1957 | Segerstad |
| 2,847,976 A | 8/1958 | Spaulding |
| 7,169,746 B2 | 1/2007 | Shoji et al. |
| 2003/0022805 A1 | 1/2003 | Clare |
| 2003/0036489 A1 | 2/2003 | Liu et al. |
| 2011/0130323 A1* | 6/2011 | Behan ................. C11B 9/00 512/13 |
| 2012/0004498 A1 | 1/2012 | Malaspina et al. |
| 2015/0164764 A1* | 6/2015 | Bonnet ................. A61K 8/602 514/777 |

FOREIGN PATENT DOCUMENTS

| CN | 103387872 A | 11/2013 | |
| JP | 2002-336337 A | 11/2002 | |
| JP | 2003-073249 A | 3/2003 | |
| JP | 2003-105669 A | 4/2003 | |
| JP | 2005-179396 A | 7/2005 | |
| JP | 2006-22119 A | 1/2006 | |
| JP | 2008-505188 A | 2/2008 | |
| JP | 2008-169334 A | 7/2008 | |
| JP | 2013-513720 A | 4/2013 | |
| JP | 2014-005404 A | 1/2014 | |
| JP | 2014-047245 A | 3/2014 | |
| JP | 2015-535536 A | 12/2015 | |
| KR | 20080096995 A * | 11/2008 | |
| WO | WO 02/49600 A1 | 6/2002 | |
| WO | WO-02089862 A2 * | 11/2002 | ............. A61L 9/014 |
| WO | WO 2009/052643 A1 | 4/2009 | |
| WO | WO 2012/173464 A1 | 12/2012 | |

OTHER PUBLICATIONS

U.S. Appl. No. 16/311,054, filed Dec. 18, 2018.
Faturi et al., "Anxiolytic-like effect of sweet orange aroma in Wistar rats," Progress In Neuro-Psychopharmacology & Biological Psychiatry, 34:605-609 (2010).
International Search Report dated Aug. 21, 2017 in International Application No. PCT/US2017/040064.
International Search Report dated Oct. 6, 2017 in International Application No. PCT/US2017/040070.
Komori et al., "Effects of Citrus Fragrance on Immune Function and Depressive States," Neuroimmunomodulation 2:174-180 (1995).
Kumar, "Chemical Composition of Essential Oil Isolated from the Rhizomes of Kaempferia Galanga L.," Int J Pharm Bio Sci 5(1):225-231 (2014).
Majnooni, et al., "Chemical composition and anxiolytic evaluation of *Achillea wilhelmsii* C. Koch essential oil in rat," Res Pharm Sci. 8(4):269-275 (2013).

(Continued)

*Primary Examiner* — Bong-Sook Baek
(74) *Attorney, Agent, or Firm* — Baker Botts L.L.P.

(57) ABSTRACT

A fragrance composition comprising one or more fragrance compounds for use in reducing or inhibiting a subject's physiological reaction to stress is disclosed. The composition can be incorporated into various consumer end products.

11 Claims, No Drawings

(56) References Cited

OTHER PUBLICATIONS

Setzer, "Essential oils and Anxiolytic Aromatherapy," Natural Product Communications 4(9):1305-1316 (2009).

Shah et al., "Scientific basis for the therapeutic use of *Cymbopogon citratus*, stapf (Lemon grass," Journal of Advanced Pharmaceutical Technology & Research 2(1):3-8 (2011).

Anwar et al., "Antioxidant and antimicrobial activities of essential oil and extracts of fennel (*Foeniculum vulgare* Mill.) seeds from Pakistan," Flavour and Fragrance Journal 24:170-176 (2009).

\* cited by examiner

FRAGRANCE COMPOSITIONS AND METHODS OF USE THEREOF

CROSS-REFERENCE TO RELATED APPLICATION

This application is a U.S. National Stage Patent Application under 35 U.S.C. § 371 of International Application No. PCT/US2017/040070, filed on Jun. 29, 2017, which claims priority to U.S. Provisional Application No. 62/356,516, filed on Jun. 29, 2016, the contents of each of which are incorporated by reference herein in their entirety.

FIELD

The present disclosure relates to fragrance compositions that can be administered to reduce or inhibit a subject's response to stress.

BACKGROUND

Stress is the human body's reaction to internal or external stimuli. It is well documented that stress typically causes a negative impact on a person's mental and physical health. Long-term, or chronic stress has been linked to anxiety, depression, heart problems, weight gain, sleep disorders, and memory and concentration impairment. Numerous pharmaceutical remedies exist to treat or lessen these stress responses. However, there remains a need for alternative remedies and solutions.

Mankind has used odors throughout history for a multitude of purposes, including therapeutic purposes. Folk remedies of many ancient civilizations call for the use of plant and animal scents. Despite the diminished use of such therapies with the advent of modern medicine, there is clear scientific evidence confirming the effect of odors on the functioning of the autonomic nervous system as well as the neuroendocrine system. This is because they are detected by the Jacobson-organ in the nasal septum and enter directly into the limbic system, the center of the brain linked to moods and emotions, which unconsciously affects the functions of inner organs.

It is desirable to create fragrances which can be used in consumer products to lessen the stress response in consumers. Therefore, there remains a need to identify fragrance compounds and fragrance accords that effectively impact an individual's reaction to stress, and create fragrance compositions comprising such compounds and accords. The present disclosure addresses this need as disclosed in further detail below.

SUMMARY OF THE INVENTION

The present disclosure relates to fragrance compositions comprising at least one compound that effectively reduces or inhibits physiological responses to stress. Specifically, the present disclosure is directed to compositions comprising at least one compound and a method of using such compositions to reduce or inhibit a subject's response to stress.

In certain embodiments, the fragrance composition comprises at least one fragrance compound selected from the group consisting of ambroxide, bornyl acetate L, camphor, citral, citronellal, citronellol, 3-(4-Isopropylphenyl)-2-methylpropanal, 2,4-Di(tert-butyl)-cyclohexan-1-one, dihydromyrcene, dihydromyrcenyl acetate, eucalyptol, myrcenyl acetate, 1-(1,2,3,4,5,6,7,8-Octahydro-2,3,8,8,-tetramethyl-2-naphthyl)ethan-1-one, 2,5,5-Trimethyl-1,3,4,4a,6,7-hexahydronaphthalen-2-ol, (1,7,7-Trimethylbicyclo[2.2.1]hept-2-yl)-cyclohexanol, 2-tert-Butylcyclohexyl acetate, 1-Cyclooct-4-enyl methyl carbonate, and combinations thereof.

In certain embodiments, the fragrance composition comprises from about 0.001 wt % to about 100 wt % fragrance compounds. In certain embodiments, the fragrance composition comprises from about 0.001 wt % to about 10 wt % fragrance compounds.

In certain embodiments, the fragrance composition comprises citral, citronellol, eucalyptol, myrcenyl acetate, and 1-(1,2,3,4,5,6,7,8-Octahydro-2,3,8,8,-tetramethyl-2-naphthyl)ethan-1-one. In certain embodiments, the fragrance composition comprises ambroxide, citronellol, 3-(4-isopropylphenyl)-2-methylpropanal, myrcenyl acetate, (1,7,7-trimethylbicyclo[2.2.1]hept-2-yl)-cyclohexanol, and 2-tert-butylcyclohexyl acetate.

In certain embodiments, the fragrance composition comprises from about 1 wt % to about 80 wt % eucalyptol. In certain embodiments, the fragrance composition comprises from about 2 wt % to about 82 wt % camphor. In certain embodiments, the fragrance composition comprises from about 1 wt % to about 31 wt % bornyl acetate L. In certain embodiments, the fragrance composition comprises from about 1 wt % to about 40 wt % citronellol. In certain embodiments, the fragrance composition comprises from about 1 wt % to about 80 wt % citronellal.

The present disclosure also provides a consumer product comprising a fragrance composition.

The presently disclosed subject matter also provides for a method of reducing or inhibiting a stress response in a subject in need thereof by administering the composition disclosed herein to the subject in an amount effective to reduce or inhibit a response to stress stimuli. In certain embodiments, the fragrance composition is administered before, during, or after exposure to the stress stimuli.

DETAILED DESCRIPTION

As discussed above, there is a need in the art to identify novel fragrances and accords that effectively impact a subject's reaction to stress so as to provide an effective composition for treatment or prevention of stress responses. The presently disclosed subject matter addresses this need through a fragrance composition comprising at least one compound that can be administered to a subject to effectively reduce or inhibit stress.

1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosure and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within three or more than three standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within five-fold, and more preferably within two-fold, of a value.

As used herein, the term "fragrance sample" is taken to mean any individual material, e.g., a fragrance composition (which is synonymous with perfume ingredient and perfume material), which can contain one or more accords. It is also understood that a "fragrance sample" can be a mixture of individual materials, such as, for example, multiple accords or a fully formulated fragrance.

As used herein, the term "accord" refers to a formulation that contains one or more different compounds that creates a specific smell, odor or scent, and that causes a specific physiological effect when used in proper effective amounts as necessary.

As used herein, the term "stressor" and "stress stimuli" are used interchangeably and refer to one of more event(s) which induces a stress response in a subject. The stressor can be chemical, biological, environmental, or another external stimulus that causes a stress reaction within a subject's body.

As used herein, the term "subject" refers to a human or a non-human subject. Non-limiting examples of non-human subjects include non-human primates, dogs, cats, mice, rats, guinea pigs, rabbits, pigs, fowl, horses, cows, goats, sheep, cetaceans, etc.

As used herein, the term "treat" or "treating" refers to intervention to alter (e.g., lower) the stress level of the subject, e.g., by administering a fragrance composition.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "inhibit" or "prevent" refers to the ability of compound or composition, e.g., a fragrance composition, to stop, decrease, or reduce stress within a subject.

As used herein, the term "enantiomers" refers to a pair of stereoisomers that are non-superimposable mirror images of each other. A 1:1 mixture of a pair of enantiomers is a "racemic" mixture. The term is used to designate a racemic mixture where appropriate.

As used herein, the term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextrorotatory or levorotatory) which they rotate plane polarized light at the wavelength of the sodium D line. The compounds of the presently disclosed subject matter contain one or more asymmetric centers and can thus give rise to enantiomers, diastereomers, and other stereoisomeric forms that can be defined, in terms of absolute stereochemistry, as (R)- or (S)-. The presently disclosed subject matter is meant to include all such possible isomers, including racemic mixtures, optically pure forms and intermediate mixtures. Optically active (R)- and (S)-isomers can be prepared using chiral synthons or chiral reagents, or resolved using conventional techniques. If the compound contains a double bond, the substituent can be E or Z configuration. If the compound contains a disubstituted cycloalkyl, the cycloalkyl substituent can have a cis- or trans-configuration. All tautomeric forms are also intended to be included.

As used herein, the term "isomers" refers to different compounds that have the same molecular formula but differ in arrangement and configuration of the atoms. Also as used herein, the term "stereoisomer" refers to any of the various stereo isomeric configurations which can exist for a given compound of the presently disclosed subject matter and includes geometric isomers. It is understood that a substituent can be attached at a chiral center of a carbon atom. Therefore, the presently disclosed subject matter includes enantiomers, diastereomers or racemates of the compound. Also as used herein, the terms "constitutional isomers" refers to different compounds which have the same numbers of, and types of, atoms but the atoms are connected differently.

2. Fragrance Compounds

The fragrance compositions of the presently disclosed subject matter comprise one or more fragrance compounds. Although structurally diverse, each fragrance compound gives an odor, and the various compounds can be used alone or in combination. Because of their pleasant odor character, fragrance compounds can be incorporated into various product applications. Surprisingly, the subject disclosure explains that it has been unexpectedly discovered that certain compounds act on the autonomic nervous system or the hypothalamus-pituitary-adrenal (HPA) axis to effectively treat, reduce, inhibit, or prevent stress responses.

Fragrance compounds can include, but are not limited to, ambroxide, bornyl acetate L, camphor, citral, citronellal, citronellol, 3-(4-isopropylphenyl)-2-methylpropanal, 2,4-di(tert-butyl)-cyclohexan-1-one, dihyrdomyrcene, dihydromyrcenyl acetate, eucalyptol, myrcenyl acetate, 1-(1,2,3,4,5,6,7,8-octahydro-2,3,8,8,-tetramethyl-2-naphthyl)ethan-1-one, 2,5,5-trimethyl-1,3,4,4a,6,7-hexahydronaphthalen-2-ol, (1,7,7-trimethylbicyclo[2.2.1]hept-2-yl)-cyclohexanol, 2-tert-butylcyclohexyl acetate, and 1-cyclooct-4-enyl methyl carbonate.

In certain embodiments, the present disclosure provides fragrance compounds that can include eucalyptol and 3-(4-isopropylphenyl)-2-methylpropanal, as well as constitutional isomers, enantiomers, stereoisomers, and racemic mixtures of said compounds listed herein. Non-limiting examples of compounds are further described, for example, in www.thegoodscentscompany.com.

In specific embodiments, the one or more compounds (taken alone or together) make up a fragrance accord. In one embodiment, one compound makes up the accord. In another embodiment, two compounds make up the accord. In another embodiment, three compounds make up the accord. In another embodiment, four or more compounds make up the accord. These accords are then used in fragrance compositions as discussed in more detail below.

3. Fragrance Compositions

The compounds and accords of the presently disclosed subject matter can be formulated into different fragrance compositions. As discussed above, each accord contains at least one fragrance compound. A fragrance composition in accordance with the presently disclosed subject matter can include one or more, two or more, or three or more of the fragrance compounds described above.

In certain embodiments, the one or more compounds of the present disclosure are formulated in a composition at a concentration from about 0.001% to about 100% by weight, or from about 0.01% to about 90% by weight, or from about 0.1% to about 80% by weight, or from about 1% to about 70% by weight, or from about 2% to about 60% by weight, or from about 5% to about 50% by weight, or from about 5% to about 40% by weight, or from about 5% to about 30% by weight, or from about 5% to about 20% by weight, or from about 5% to about 10% by weight of the total fragrance composition. In certain embodiments, the fragrance compositions of the present disclosure contain at least about 5%, at least about 10%, at least about 20%, or at least about 25% by weight of a fragrance accord.

In certain embodiments, the one or more compounds of the present disclosure are formulated in a composition at a concentration of about 5%, about 10%, about 20%, about 30%, about 40%, about 50%, about 60%, about 70%, about 80%, or about 90% by weight of the fragrance accord.

In certain embodiments, the one or more compounds of the present disclosure are formulated in a composition at a concentration from about 0.01% to about 20%, or from about 0.01% to about 10%, or from about 0.01% to about 5%, or from about 0.01% to about 1%, or from about 0.01% to about 0.5%, or rom about 0.01% to about 0.2% by weight of the fragrance accord.

In certain embodiments, the fragrance compositions of the present disclosure contain at least about 98.5% by weight of a fragrance accord. In one embodiment, the fragrance composition contains 100% by weight of a fragrance accord.

A fragrance composition includes, but is not limited to, one or more fragrance accords, and/or one or more additional fragrance compounds. A fragrance composition can further include one or more additional fragrance accords or compounds. In certain embodiments, the additional fragrance accords or compounds can be, but are not limited to, one or more aldehydic compound(s), one or more balsamic compound(s), one or more citrus compound(s), one or more floral compound(s), one or more fruity compound(s), one or more gourmand compound(s), one or more green compound(s), one or more marine compound(s), one or more mossy compound(s), one or more musk compound(s), one or more piney compound(s), one or more powdery compound(s), one or more spicy compound(s), one or more woody compound(s), one or more herbal compound(s), and/or one or more camphoraceous compound(s), or combinations thereof.

Presently disclosed fragrance accords or compounds can be classified into one or more of the aforementioned compound categories (i.e., aldehydic, floral, fruity, herbal, woody, spicy, camphoraceous, etc.) depending on the amount or level of use in a fragrance composition.

An herbal compound can be p-menthane-3,8-diol and/or terpinyl acetate.

A camphoraceous compound can be borneol, bornyl isobutyrate, camphor, fenchone, menthol (e.g., menthol L), and/or rosemary oil.

An aldehydic compound can be aldehyde c-12 MNA.

A balsamic compound can be isopropoxy ethyl salicylate and/or benzy salicylate.

A citrus compound can be citral, citronellal, citronellol (e.g., L-citronellol), decanal, limonene, myrcenol, myrcenol acetate, nootkatone, sinensal, bergamot oil, grapefruit oil, lemon oil, lime oil, and/or orange oil.

A floral compound can be anisyl acetate, anisic aldehyde, benzyl acetate, 3-(4-tert-butylphenyl)propanal, butyl acetate, 3-(4-isopropylphenyl)-2-methylpropanal, cyclohexyl lactone, δ-damascone, farnesal, L-farnesal, farnesol, florhydral, floralozone, geraniol, gernayl acetate, piperonal, hedione, heliobouquet, hexyl cinnamaldehyde, hexyl salicylate, indole, α-ionone, β-ionone, isopropoxy ethyl salicylate, jasmodione, cis-jasmone, kovanol, laurinol, linalool, linalyl acetate, mayol, methyl dihydrojasomante, γ-methyl ionone, methoxymelonal, nerol, nerolione, neryl acetate, 2-pentyl cyclopentanone, phenoxanol, phenoxy ethyl isobutyrate, phenylacetaldehyde, phenyl ethyl alcohol, rose oxide, suzaral, undecavertol, geranium oil, lavender oil, rose oil, and/or ylang oil.

In certain embodiments, the one or more floral compounds include, but are not limited to, cis jasmone [CAS No. 488-10-8], citronellol L [CAS No. 7540-51-4], citronellyl acetate L [CAS No. 150-84-5], 3-(4-propan-2-ylphenyl) butanal [CAS No. 103-95-7], 1-(2,6,6-trimethyl-1-cyclohex-3-enyl)but-2-en-1-one [CAS No. 57378-68-4], decatone [CAS No. 34131-98-1], dimethyl benzyl carbinyl acetate [CAS No. 151-05-3], ionone alpha [CAS No. 127-41-3], Jasmodione® [CAS No. 24851-98-7], 1-dihydro citronellol [CAS No. 106-21-8], 1-dihydro farnesol [CAS No. 51411-24-6], linalool [CAS No. 78-70-6], linalyl acetate [CAS No. 115-95-7], Lorexan® [CAS No. 5182-36-5], meth ionone gamma [CAS No. 127-51-5], nerol [CAS No. 106-25-2], neryl acetate [CAS No. 141-12-8], raspberry ketone [CAS No. 5471-51-2], 1-(3,3-dimethylcyclohexyl)ethyl acetate [CAS No. 25225-10-9], 4-methyl-2-(2-methylprop-1-enyl)oxane [CAS No. 16409-43-1], Sakura Salicylate™ [CAS No. 79915-74-5], Thesaron® [CAS No. 22471-55-2], Trepanol® [CAS No. 13019-22-2], and combinations thereof.

A fruity compound can be aldehyde C16, allyl caproate, allyl cyclohexyl proprionate, allyl heptanoate, amyl acetate, benzaldehyde, L-citronellyl acetate, L-citronellyl nitrile, cyclacet, damascenone, β-decalactone, γ-decalactone, diethyl malonate, dimethyl phenyl ethyl carbinol, dimethyl sulfide, γ-dodecalactone, ethyl acetate, ethyl butyrate, ethyl caproate, ethyl decadienotate, ethyl-2-methylbutyrate, ethyl acetoacetate, ethyl propionate, florol, hexyl acetate, hexyl isobutyrate, isoamyl acetate, jasmolactone, manzanate, melonal, methyl heptyl ketone, γ-nonalactone, γ-octalactone, phenyl ethyl isobutyrate, raspberry ketone, ringonol, thesaron, tolyl aldehyde, γ-undecalactone, vanoris, 2-(2-(4-methyl-3-cyclohexen-1-yl)propyl)cyclopentanone, and/or 2-tert-butylcyclohexyl acetate.

A gourmand compound can be caprylic acid, coumarin, ethyl fraison, ethyl vanillin, ethyl maltol (e.g., Veltol Plus), filbertone, furaneol, guaiacol, maple furanone, 2-acetyl pyrazine, 2,5-dimethyl pyrazine, and/or vanillin.

A green compound can be dynascone, galbanolene, trans-2-hexenal, cis-3-hexenol, hexen-1-ol, cis-3-hexenyl acetate, cis-3-hexenyl butyrate, cis-3-hexenyl salicylate, liffarome, methyl octine carbonate, 2,6-nonadienal, oxane, stemone, styrallyl acetate, triplal, undecavertol, violet methyl carbonate (e.g., 1-cyclooct-4-enyl methyl carbonate), vionil, and/or violet leaf extract.

A marine compound can be myrac aldehyde and/or Calone 1951.

A mossy compound can be oakmoss #1.

A musk compound can be ambrettolide, ambretone, ambroxide, exaltolide, galaxolide, habanolide, helvetolide, (1'R)-3-methyl-5-(2,2,3-trimethylcyclopentan-1-yl)-2-pentanone, muscenone, musk T, L-muscone, and/or tonalid.

A piney compound can be β-pinene, terpineol, and/or alpha-terpineol.

A powdery compound can be heliotropine and/or whiskey lactone (methyl octalactone).

A spicy compound can be β-caryophellene, cinnamaldehyde, cuminaldehyde, eugenol, isoeugenol, perilla aldehyde, cardamom oil, clove oil, ginger extract, and/or black pepper extract.

A woody compound can be amber core, amber extreme, ambroxide, bacdanol, bornyl acetate, cedramber, cedanol, ebanol, hindinol, hinokitiol, javanol, norlimbanol dextro, osyrol, patchone, 2,5,5-trimethyl-1,3,4,4a,6,7-hexahydronaphthalen-2-ol, α-pinene, β-pinene, sandalmysore core, sandalore, (1,7,7-trimethylbicyclo[2.2.1]hept-2-yl)-cyclohexanol, 1-(1,2,3,4,5,6,7,8-octahydro-2,3,8,8,-tetramethyl-2-naphthyl)ethan-1-one, cedarwood oil, patchouli oil, sandalwood oil, and/or vetiver oil.

In certain embodiments, the one or more woody compounds include, but are not limited to, cedarwood oil [CAS No. 68990-83-0, 8000-27-9 & 8023-85-6], Hindinol® [CAS No. 28219-60-5], Levosandol® [CAS No. 28219-61-6], Nopol T [CAS No. 128-50-7], Orbitone® [CAS No. 54464-57-2], patchouli oil [CAS No. 8014-09-3], sandalwood oil [CAS No. 8006-87-9 & 8024-35-9], Santalex® T [CAS No. 68877-29-2], vertivert oil [CAS No. 8016-96-4], (R)-2,3,4,7,8,8a-hexahydro-3,6,8,8-tetramethyl-5-acetyl-1H-3a,7-methanoazulene [CAS No. 32388-55-9], vetiver extract [CAS No. 84238-29-9], and combinations thereof.

In certain embodiments, the one or more amber compounds include, but are not limited to, Ambrinol 20-T [CAS No. 41199-19-3], 1-(2-tert-butylcyclohexyl)oxybutan-2-ol [CAS No. 139504-68-0], (4aR,5R,7aS,9R)-octahydro-2,2,5,8,8,9a-hexamethyl-4h-4a,9-methanoazuleno(5,6-d)-1,3-dioxole [CAS No. 211299-54-6], 5-butan-2-yl-2-(2,4-dimethyl-1-cyclohex-3-enyl)-5-methyl-1,3-dioxane [CAS No. 117933-89-8], Norlimbanol [CAS No. 70788-30-6], and combinations thereof.

Additional fragrance compounds, including but not limited to, one or more of the compounds disclosed herein, can also be included in the compositions so long as the addition does not change the ability of the composition to treat, reduce, inhibit or prevent stress responses.

In certain embodiments, the additional fragrance compounds are formulated in a composition at a concentration from about 0.001% to about 99% by weight, or from about 0.01% to about 90% by weight, or from about 0.1% to about 80% by weight, or from about 1% to about 70% by weight, or from about 2% to about 60% by weight, or from about 5% to about 50% by weight, or from about 10% to about 40% by weight, or from about 15% to about 30% by weight, or from about 20% to about 25% by weight.

In certain embodiments, the fragrance compositions of the present disclosure include one or more fragrance accords. In certain embodiments, each fragrance accord can comprise two or more fragrance compounds.

In certain embodiments, fragrance compositions can comprise one or more fragrance compounds through the use of essential oils containing such fragrance compounds. Likewise, fragrance accords can be compounds of essential oils or comprise essential oils. Essential oils are concentrated hydrophobic liquids containing volatile aromatic compounds from plants. Many essential oils can contain certain amounts of, for example, limonene, terpineol, terpinyl acetate, eucalyptol, ambroxide, bornyl acetate L, camphor, citronellal, citronellol, or other fragrance compounds disclosed herein.

Essential oils can contain eucalyptol. For example, bay oil comprises about 1.5% by weight eucalyptol and eucalyptus oil comprises about 78.5% by weight eucalyptol Essential oils can contain camphor. For example, coriander oil comprises about 3% by weight camphor and petitgrain combava oil comprises about 81.49% by weight camphor.

Essential oils can contain bornyl acetate L. For example, fir oil (or fir needle oil) comprises about 5.4% or about 30.96% by weight bornyl acetate L and pine oil comprises about 26% by weight bornyl acetate L.

Essential oils can contain cintronellol. For example, chamomile comprises about 1.9% by weight citronellol and rose essence comprises about 35.2% by weight citronellol.

Essential oils can contain citronellal. For example, petitgrain oil citronier comprises about 1.38% by weight citronellal, citronella oil comprises about 32.3% by weight citronellal, and eucalyptus citriodora oil comprises about 80.1%.

In certain embodiments, a fragrance composition comprises from about 1 wt % to about 80 wt % eucalyptol.

In certain embodiments, a fragrance composition comprises from about 2 wt % to about 82 wt % camphor.

In certain embodiments, a fragrance composition comprises from about 1 wt % to about 31 wt % bornyl acetate L.

In certain embodiments, a fragrance composition comprises from about 1 wt % to about 40 wt % citronellol.

In certain embodiments, a fragrance composition comprises from about 1 wt % to about 80 wt % citronellal.

In certain embodiments, a stress inhibiting fragrance accord comprises about 60% by weight of a citrus compound(s), and about 40% by weight of a woody compound(s). In one embodiment, a stress inhibiting fragrance accord comprises about 10% by weight citral, about 20% by weight citronellol, about 16% by weight eucalyptol, about 14% by weight myrcenyl acetate, and about 40% by weight 1-(1,2,3,4,5,6,7,8-octahydro-2,3,8,8,-tetramethyl-2-naphthyl)pethan-1-one.

In certain embodiments, a stress inhibiting fragrance accord comprises about 4% by weight of a musk/woody compound(s), about 30% by weight of a citrus compound(s), about 10% by weight of a floral compound(s), about 40% by weight of a woody compound(s), and about 16% by weight of a fruity compound(s). In one embodiment, a stress inhibiting fragrance accord comprises about 4% by weight ambroxide, about 20% by weight citronellol, about 10% by weight 3-(4-isopropylphenyl)-2-methylpropanal, about 10% by weight myrcenyl acetate, about 40% by weight (1,7,7-trimethylbicyclo[2.2.1]hept-2-yl)-cyclohexanol, and about 16% by weight 2-tert-butylcyclohexyl acetate.

In certain embodiments, a stress inhibiting fragrance accord comprises about 4% by weight of a musk compound(s), about 10% by weight of a floral compound(s), about 10% by weight of a citrus compound(s), about 60% by weight of a woody compound(s), and about 16% of a fruity compound(a). In one embodiment, a stress inhibiting fragrance accord comprises about 4% by weight ambroxide, about 10% by weight 3-(4-isopropylphenyl)-2-methylpropanal, about 10% by weight myrcenyl acetate, about 20% by weight Iso E Super, about 40% by weight (1,7,7-Trimethylbicyclo[2.2.1]hept-2-yl)-cyclohexanol mixture, and about 16% by weight 2-tert-butylcyclohexyl acetate.

In certain embodiments, a stress inhibiting fragrance accord comprises about 40% by weight of a woody compound(s), about 20% of a piney compound(s), about 10% by weight of a citrus compound(s), and about 30% of a fruity compound(a). In one embodiment, a stress inhibiting fragrance accord comprises about 10% by weight bornyl acetate L, about 20% by weight alpha terpineol, about 10% by weight myrcenyl acetate, about 10% 2-(2-(4-methyl-3-cyclohexen-1-yl)propyl)cyclopentanone, about 30% (1,7,7-Trimethylbicyclo[2.2.1]hept-2-yl)-cyclohexanol mixture, and about 20% 2-tert-butylcyclohexyl acetate.

In certain embodiments, a stress inhibiting fragrance accord comprises about 4% by weight of a musk compound(s), about 10% by weight of a piney compound(s), about 50% by weight of a woody compound(s), about 20% by weight of an herbal compound(s), and about 16% of a fruity compound(a). In one embodiment, a stress inhibiting fragrance accord comprises about 4% by weight ambroxide, about 10% by weight alpha terpineol, about 50% by weight (1,7,7-Trimethylbicyclo[2.2.1]hept-2-yl)-cyclohexanol mixture, about 20% by weight terpinyl acetate, and about 16% by weight 2-tert-butylcyclohexyl acetate.

In certain embodiments, a stress inhibiting fragrance accord comprises about 40% by weight of a woody compound(s), about 20% by weight of a citrus compound(s), and about 40% by weight of a fruity compound(s). In one embodiment, a stress inhibiting fragrance accord comprises about 10% by weight bornyl acetate, about 20% by weight myrcenyl acetate, about 20% by weight 2-(2-(4-methyl-3-cyclohexen-1-yl)propyl)cyclopentanone, about 30% by weight (1,7,7-Trimethylbicyclo[2.2.1]hept-2-yl)-cyclohexanol mixture, and about 20% by weight 2-tert-butylcyclohexyl acetate.

In certain embodiments, a stress inhibiting fragrance accord comprises about 8% by weight of a musk compound(s), about 50% by weight of a woody compound(s), about 40% by weight of a fruity compound(s), and about 2% by weight of a green compound(s). In one embodiment, a stress inhibiting fragrance accord comprises about 8% by weight ambroxide, about 50% by weight (1,7,7-Trimethylbicyclo[2.2.1]hept-2-yl)-cyclohexanol mixture, about 40% by weight 2-tert-butylcyclohexyl acetate, and about 2% by weight 1-cyclooct-4-enyl methyl carbonate.

4. Use of Compositions in Consumer Products

In certain embodiments, the compositions of the present disclosure are formulated as part of a consumer product.

The compositions of the presently disclosed subject matter relate to fragrance formulations, and/or a flavor formulations, in which the compositions are blended as a calming or sedative effect-providing fragrance and/or flavor modifier, and the fragrance and/or flavor formulation can be used in, for example, perfumes, colognes, shampoos, rinses, skin cares, body shampoos, body rinses, body powders, air fresheners, deodorants, baths, foods, snacks, beverages, and the like, if necessary in combination with auxiliary materials.

In certain embodiments, the consumer products of the present disclosure can be, but are not limited to, air care products (e.g., candles, aerosols, air fresheners, liquid electric air fresheners, fragrance diffusers, gel air fresheners, plug-in air fresheners, etc.); home care products (e.g., laundry detergents, softeners, cleaners, dryer sheets, etc.); personal care products (e.g., lotions, creams, body washes, hand soaps, shampoos, conditioners, soaps, etc.); sanitary products (e.g., towels, toilet paper, tissue paper, wet tissue paper, handkerchiefs, wet towels, etc.); pet care products; fine fragrance (e.g., parfum, eau de parfum, colognes, eau de toilette, etc.); auto care products (e.g., cleaners, air fresheners, wipes, soaps, etc.); cosmetics (e.g., skin cream, cleansing cream, night cream, hand cream, lotion, after-shave lotion, body lotion, foundation, lip stick, lip cream, nail polish, nail polish remover, talcum powder, anti-wrinkle and/or anti-aging cosmetics, sun protection products, massage oil, etc.); hair cosmetics (e.g., shampoo, rinse, conditioner, rinse in shampoo; hair styling agents such as pomade, hair tonic, hair gel, hair cream and hair mousse; hair growing agents; hair coloring agents; etc.); bath agents (e.g., powder bath additives, solid foaming bath additives, bath oils, bubble bath aroma generators, bath salts, etc.); writing products (e.g., pens, crayons, paints, pencils, paper, origami, seals, etc.); products for play (e.g., balls, beanbags, cards, tops, dolls, building blocks, etc.); flavored products (e.g., confections, beverages, snacks, prepared meals, OTC medications, gum, etc.); pharmaceuticals (e.g., plasters, ointments, suppositories, tablets, liquid medicines, capsules, granules, etc.); foods and drinks or beverage (e.g., confectioneries consisting of gum, candy, snacks such as potato crisps, baked sweets such as cookies and biscuits; drinks including refreshing drinks such as flavored tea, herb tea, juice, soda and powdered drink, fancy drinks such as tea and coffee, and milk drinks; frozen desserts such as ice cream, sherbet, mousse, and frozen yogurt; desserts such as custard pudding, jelly, bavarois, yogurt, and cream; cooked foods such as soup, curry and stew; seasonings such as condensed soup for noodles, dressing, and mayonnaise; bakery products such as bread and donuts; daily products such as butter cream and margarine; fish paste products; etc.); and oral health products (e.g., tooth paste, oral wash, etc.).

In certain embodiments, the disclosed subject matter provides for use of the compositions described herein in a consumer product as described herein.

In certain embodiments, the compositions are formulated as part of a product to reduce stress.

In certain embodiments, the compositions are formulated as part of a product which is relaxing or sedating.

In certain embodiments, the subject disclosure relates to methods of incorporating stress-reducing or stress-inhibiting effects into a consumer product. In certain embodiments, methods include (a) providing at least one consumer product, and (b) combining the consumer product with a composition comprising at least one, two, three, or four fragrance compounds. In certain embodiments, such a composition is administered before, during, or after exposure to a stress stimuli. For example, in one non-limiting embodiment a consumer product can be combined with a composition containing eucalyptol and/or 3-(4-isopropylphenyl)-2-methylpropanal.

In one embodiment, at least a composition comprising one, two, three, or four compounds can be added to a consumer product, such as an air care product, to reduce the level of stress in a subject using the product as compared to the level of stress of a subject using a consumer product which does not comprise the subject composition. For example, a composition comprising two compounds may be added to a consumer product, such as an air freshener, which is utilized by a subject before exposure to a stressor and effectively reduces the subject's stress.

The concentration of the composition admixed with the consumer product to reduce or inhibit stress in a consumer can change based on a number of variables, for example, the specific consumer product, the physical form of the consumer product (e.g., liquid, gas, or solid) and what fragrance compounds are already present in the consumer product and the concentrations thereof.

A broad range of concentrations of the composition can be employed to reduce or inhibit the level of stress in a consumer. In certain embodiments of the present disclosure, the composition is admixed with a consumer product and the composition is present in the consumer product in an amount from about 1 to about 9000 ppm, or from about 5 to about 7500 ppm, or from about 10 to about 5000 ppm, or from about 50 to about 2500 ppm, or from about 100 to 1000 ppm, or from about 250 to 500 ppm, and any value in between.

In certain embodiments of the present disclosure, the composition is admixed with a consumer product wherein the composition is present in an amount from about 0.0001% to about 90% by weight, or from about 0.001% to about 75% by weight, or from about 1% to about 50% by weight, or from about 5% to about 25% by weight, or from about 10% to about 15% by weight, and values in between.

In certain embodiments, the composition admixed with the consumer product comprises eucalyptol or 3-(4-isopropylphenyl)-2-methylpropanal, or a combination thereof of at least one, or at least two, or at least three compounds.

In certain embodiments, the fragrance composition additionally includes one or more bases, solvents, and combinations thereof.

In certain embodiments, bases can include, but are not limited to, essential oils, lactones, aldehydes, alcohols, ketones, nitriles, esters, amides, oximes, and other fragrant compounds, and perfuming co-ingredients.

In certain embodiments, the solvents can include, but are not limited to, diproplyene glycol, propylene glycol, diethphthalate (DEP), diisononyl phthalate (DINP), benzyl benzoate, benzyl alcohol, iso propyl myristate (IPM), isopropyl palmitate (IPP/Deltyl Prime), butyl stearate, dioctyl adipate, triethyl citrate, methyl hydrogenated rosinate (CAS No. 8050-15-5),
terpenes (e.g., Glidsol 100), paraffinic naphthenic solvent (e.g., LPA-170 Solvent), isoalkanes (e.g., Soltrol 170 Isoparaffin), isoparaffins, isooctadecanol (e.g., Tego Alkanol 66), phenoxyethanol, diethylene glycol monoethyl ether (Carbitol low gravity), glycol ether (Methyl Carbitol), Dipropylene Glycol Methyl Ether (e.g., Dowanol DPM), Dipropylene Glycol Methyl Ether Acetate (e.g., Dowanol DPMA), Propylene glycol methyl ether (e.g., Dowanol PM Glycol Ether), Tripropylene Glycol Methyl Ether, Diisoheptyl Phthalate (e.g., Jayflex® 77 available from Exxon), deionized or distilled water, specially denatured ethyl alcohol (e.g., SDA 40B), Dimethyl Adipate/Dimethyl Glutarate (e.g., DBE®-LVP Esters available from FLEXISOLV®), Racemic mixture (±)-2,2-dimethyl-4-hydroxymethyl-1,3-dioxolane (e.g., Augo Clean Multi Solvent), Alcohol 40B Anhydrous 200 Proof, alcohol SDA 40B 190 Proof, Triacetin, 3-Methoxy-3-methyl-1-butanol (Solfit), Benzyl Laurate, Tripropylene Glycol Methyl Ether (e.g., Dowanol TPM), Dipropylene glycol n-butyl ether (e.g., Dowanol DPNB), Dimethyl siloxane, trimethylsiloxy-terminated (e.g., Dowanol Corning 200 Fluid), Caprylic/Capric Triglycerides (e.g., Neobee M-5), propylene glycol and glyceryl oleate (e.g., Arlacel 186), Uniceth-IC20L (e.g., Arlasolve 200 L), propanediol, 1,3, Butyl Cellosolve, Hexylene glycol, Glycerine, N Methyl Stearate, Isopropyl alcohol, 2-Methyl-1,3-propanediol (e.g., MP Diol Glycol), Diethyl Citrate, Triethyl Acetyl Citrate, Isopentyldiacetate (IPD-AC), Dimethyl 2-methylpentanedioate (e.g., Rhodiasolv Iris), medium chain triglycirides (MTC), terpene hydrocarbons (e.g., Dipentene 5100), DL-limonene (e.g., Dipentene 122), 3,5,5-trimethylhexyl acetate, Diethyl Malonate, Limonene (e.g., Unitene D), cyclohexyl acetate, para-tertiary-butyl (e.g., Vertenex), Ethyl Acetate, and Diethyl Succinate.

In certain embodiments, the presently disclosed subject matter includes:
a) A consumer product comprising a sufficient amount of at least one fragrance compound to provide a concentration of said at least one compound of at least 7 nanograms per cubic foot of air, preferably from 7.4 nanograms per cubic foot of air to 28 nanograms per cubic foot of air, or more preferably 7.4 nanograms per cubic foot of air to about 27.7 nanograms per cubic foot of air. Said consumer product can be a fabric and home care product, baby care product, beauty care product, family care product, and/or a feminine care product.
b) The consumer product of Paragraph a) comprising, in addition to said at least one compound, one or more fragrance raw materials.
c) The consumer product according to Paragraphs a) or b) wherein said at least one compound is provided, at least in part, by a fragrance delivery system, preferably said fragrance delivery system is selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system. More preferably, the fragrance delivery system is a Polymer Assisted Delivery (PAD) system comprising a Polymer Assisted Delivery Reservoir system, where said Polymer Assisted Delivery Reservoir system comprises a fragrance delivery particle that comprises a shell material and a core material. The shell material encapsulates the core material, said core material comprising said at least one compound and said shell comprising a material selected from the group consisting of polymethacrylates; polyethylenes; polyamides; polystyrenes; polyisoprenes; polycarbonates; polyesters; polyacrylates; aminoplasts, preferably said aminoplast comprises a polyureas, polyurethane, and/or polyureaurethane, preferably said polyurea comprises polyoxymethyleneurea and/or melamine formaldehyde, more preferably said polyurea comprises melamine formaldehyde and/or cross linked melamine formaldehyde; polyolefins; polysaccharides, alginate and/or chitosan; gelatin; shellac; epoxy resins; vinyl polymers; water insoluble inorganics; silicone; and mixtures thereof, preferably said shell is coated by a water-soluble cationic polymer selected from the group that consists of polysaccharides, cationically modified starch and cationically modified guar, polysiloxanes, dimethyldiallylammonium polyhalogenides, copolymers of dimethyldiallylammonium polychloride and vinyl pyrrolidone, acrylamides, imidazoles, imidazolinium halogenides, and imidazolium halogenides and polyvinyl amine and its copolymers with N-vinyl formamide.
d) The consumer product according to any of Paragraphs a) through c), said consumer product comprising, based on total consumer product weight:
 1. from 0.1% to 99%, preferably from 1% to 80%, more preferably from 5% to 55%, most preferably from 10% to 50% of a solvent, preferably said solvent is selected from cyclopentasiloxane, ethanol, water, propylene glycol, dipropylene glycol, and mixtures thereof and
 2. from 0% to 30%, preferably from 0% to 20%, more preferably from 0.1% to 4%, most preferably from 0.1% to 4% of a material selected from the group consisting of a structurant, a residue masker, an antimicrobial, and mixtures thereof.

e) A consumer product according to any of Paragraphs a) through d), said consumer product comprising from 1% to 25% of an antiperspirant active selected from the group consisting of astringent metallic salts, preferably inorganic and organic salts of aluminum, zirconium, and zinc, as well as mixtures thereof, more preferably aluminum halides, aluminum chlorohydrate, aluminum hydroxyhalides, zirconyl oxyhalides, zirconyl hydroxyhalides, and mixtures thereof.

f) A consumer product according to any of Paragraphs a) or b), wherein said consumer product is a device, preferably said device is selected from the group consisting of energized air fresheners and non-energized air fresheners, more preferably said device is selected from the group consisting of:
1. wick air fresheners;
2. reservoir air fresheners;
3. porous membrane air fresheners;
4. power assisted delivery air fresheners, preferably power assisted delivery air fresheners selected from the group consisting of thermal drop-on-demand air fresheners, piezo air fresheners, heater air fresheners, fan air fresheners, or microfluidic devices air fresheners; and
5. spray devices.

g) A consumer product according to any of Paragraphs a) or b), comprising an ingredient selected from the group consisting of builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, fragrances, fragrance delivery systems, structure elasticizing agents, carriers, structurants, hydrotropes, processing aids, solvents in addition to said solubilizing agent, a fabric softener active selected from the group consisting of a silicone polymer, a polysaccharide, a clay, a fatty ester, a dispersible polyolefin, a polymer latex and mixtures thereof, pigments, and mixtures thereof.

h) A consumer product according to any of Paragraphs a) through c), said consumer product comprising, based on total consumer product weight:
1. from 0.1% to 99%, preferably from 1% to 80%, more preferably from 5% to 70%, most preferably from 10% to 50% of a solvent, preferably said solvent is selected from, water, glycerin, and mixtures thereof; and
2. from 0% to 50%, preferably from 0% to 40%, more preferably from 0.1% to 30%, most preferably from 0.1% to 15% of a material selected from the group consisting of a structurant, a humectant, a surfactant, an antimicrobial, and mixtures thereof.

i) A consumer product according to Paragraph h), said consumer product comprising, based on consumer product weight, from 3% to 30% of a surfactant, and, optionally, a miscellar phase and/or lamellar phase.

j) A consumer product according to Paragraph h), said consumer product comprising, based on consumer product weight, from 0.1% to 50% of a material selected from structurants, humectants, fatty acids, inorganic salts, antimicrobial agents, antimicrobial actives, and mixtures thereof.

k) A consumer product according to any of Paragraphs h) through j), said consumer product comprising, an ingredient selected from the group consisting of clay mineral powders, pearl pigments, organic powders, emulsifiers, distributing agents, pharmaceutical active, topical active, preservatives, surfactants, and mixtures thereof.

l) A method of reducing or inhibiting a stress response in a subject in need thereof comprising: using the consumer product of any one of Paragraphs a) through k) in an amount effective to reduce or inhibit a response to stress stimuli.

m) The method of Paragraph l), wherein the composition is used before exposure to the stress stimuli.

5. Reduction or Inhibition of Stress

In certain embodiments, the compositions of the presently disclosed subject matter are administered in an amount effective to reduce or inhibit stress in a subject.

5.1 Methods of Composition Administration

In certain embodiments of the present disclosure, the composition comprising one or more compounds is administered to a subject prior to exposure to a stressor to reduce or inhibit the subject's stress level.

In one non-limiting embodiment, the composition is administered to a subject through gaseous or volatile form. In these embodiments, the composition is administered intranasally or by inhalation. In certain embodiments, the subject inhales the composition directly or indirectly.

In further embodiments, the composition is administered via a consumer product. In one non-limiting example, the composition is admixed with a consumer product. The subject then uses the consumer product comprising the composition. Depending on the use of the consumer product, the subject is exposed to the fragrance composition.

In a specific embodiment, the composition is released into the area surrounding the subject and the subject then inhales the composition. In one non-limiting example, the composition is released into the air by a consumer product, such as an air freshener.

In certain embodiments of the present disclosure, the amount of the composition released from the consumer product is less than the total concentration of the composition admixed with the consumer product. In certain embodiments, the amount of the composition released by the consumer product, and therefore available for administration to the subject, is between about 1% and 100% of the amount of composition admixed with the consumer product. In further embodiments, the amount of composition released is between about 5% and 90%, between about 10% and 80%, between about 20% and 70%, between about 30% and 60%, and between about 40% and 50% of the amount of composition admixed with the consumer product.

5.2 Methods of Measuring Stress Relief

In certain embodiments, the compositions of the presently disclosed subject matter are administered in an amount effective to reduce or inhibit stress in a subject as determined by measuring the levels of specific hormones in a subject. In certain embodiments, the composition is incorporated into a consumer product, as discussed above, which is utilized by a subject before, during or after exposure to a stressor.

5.2.1 Biomarkers

In certain embodiments, the compositions of the presently disclosed subject matter are administered to a subject, a stressor is applied, and specific biomarkers are measured to determine the level of stress reduction or inhibition.

In specific embodiments, the compositions of the presently disclosed subject matter are effective at reducing or inhibiting stress if a change in cortisol, or salivary alpha-amylase, or both are detected. As used herein, an effective "change" refers to a decrease in salivary levels when measured before and after exposure to a test material (compound or mixture). An effective "change" also includes a minimal increase before and after exposure to a test material (compound or mixture), wherein the increase is less than a change as compared to a control solvent. The compounds or mixtures provided by the presently disclosed subject matter are effective when an effective change is noted in either salivary cortisol or salivary alpha-amylase. Each test parameter alone is considered to be indicative of stress reduction.

5.2.1.1 Cortisol

Cortisol is released by the body as part of a longer term response to stress, resulting from the activation of the hypothalamus-pituitary-adrenal (HPA) axis. A change in cortisol levels therefore indicates an subject's reaction, or lack therefor, to a stressor.

Accordingly, in certain embodiments of the subject disclosure, salivary cortisol levels are measured as biomarkers to determine an subject's reaction, or lack thereof, to a stressor. A reduction in, or maintenance of, the level of biomarker indicates that the composition reduced or inhibited stress in an subject. In certain embodiments, the subject's level of salivary cortisol is measure before and after the application of a stressor. In certain embodiments the salivary cortisol level is measured, the composition is administered, the stressor is applied and then the salivary cortisol level is measured again. The percent change in the salivary cortisol level can then be calculated.

In certain embodiments, the composition is administered to a subject in an amount effective to reduce or maintain the level of salivary cortisol in the subject when the subject is exposed to a stressor as compared to the level of salivary cortisol in the subject before exposure to the stressor. In certain embodiments, the reduction in the level of salivary cortisol is between about 1% and about 100%, or between about 2% and about 75%, or between about 5% and about 50%, or between about 10% and about 45%, or between about 15% and about 40%, or between about 20% and about 35%, or between about 25% and about 30%. In certain embodiments, the reduction in the level of salivary cortisol is between about 1% and about 50%, or between about 1% and about 40%, or between about 1% and about 30%, or between about 1% and about 20%, or between about 1% and about 10%, or between about 1% and about 5%.

5.2.1.2 Alpha-Amylase

Salivary alpha-amylase is a digestive enzyme produced in and released from the saliva glands. Levels of salivary alpha-amylase increase in response to psychological and physical stress through interactions with the autonomic nervous system. Accordingly, in certain embodiments of the subject disclosure, salivary alpha-amylase levels are measured to determine an subject's reaction, or lack thereof, to a stressor. A reduction in, or maintenance of, the level of salivary alpha-amylase indicates that the composition reduced or inhibited stress in a subject. In certain embodiments, the subject's level of salivary alpha-amylase is measured before and after the application of a stressor. In certain embodiments the salivary alpha-amylase level is measured, the composition is administered, the stressor is applied and then the salivary alpha-amylase level is measured again. The percent change in the salivary alpha-amylase level can then be calculated.

In certain embodiments, the composition is administered to a subject in an amount effective to reduce the level of salivary alpha-amylase in the subject when the subject is exposed to a stressor as compared to the level of salivary alpha-amylase in the subject before, during, or after exposure to the stressor.

In certain embodiments, the reduction in the level of salivary alpha-amylase is between about 15% and about 200%, or between about 20% and about 180%, or between about 25% and about 160%, or between about 30% and about 140%, or between about 35% and about 120%, or between about 40% and about 115%, or between about 45% and about 110%, or between about 50% and about 105%, or between about 50% and about 100%, or between about 55% and about 95%, or between about 60% and about 90%, or between about 65% and about 85%, or between about 70% and about 80%.

In certain embodiments, the reduction in the level of salivary alpha-amylase is at least about 2%, about 5%, about 7.5%, about 10%, about 15%, or about 20%.

In certain embodiments, the reduction in the level of salivary alpha-amylase is between about 2% and about 100%, or between about 2% and about 75%, or between about 2% and about 50%, or between about 2% and about 40%, or between about 2% and about 30%, or between about 2% and about 20%, or between about 5% and about 20%.

6. Fragrance Delivery Systems

The benefits of the fragrance compounds disclosed herein can be further enhanced by employing a delivery system to apply such fragrance compounds. Such delivery systems include, but are not limited to, the following: polymer assisted delivery (PAD); matrix systems; reservoir systems (e.g., core-shell technology); molecule-assisted delivery (MAD); cyclodextrin (CD); starch encapsulated accord (SEA); and zeolite and inorganic carrier (ZIC). Suitable processes for employing such delivery systems are well known in the art.

In one aspect, a fragrance delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, wherein said fragrance delivery system can comprise a fragrance compound disclosed in the present disclosure.

7. Processes of Making and Using Consumer Products

The embodiments of consumer products of the present disclosure can be formulated into any suitable form and prepared by any process chosen by the formulator.

7.1 Fabric/Home Care: Cleaning and/or Treatment Compositions

In one aspect of the presently disclosed consumer product, said consumer product is a cleaning and/or treatment composition, typically comprising an ingredient selected from the group consisting of builders, chelating agents, dye transfer inhibiting agents, dispersants, enzymes, enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, fragrances, fragrance delivery systems, structure elasticizing agents, carriers, structurants, hydrotropes, processing aids, solvents in addition to said solubilizing agent, a fabric softener active selected from the group consisting of a quarternary ammonium compound, a silicone polymer, a polysaccharide, a clay, an amine, a fatty ester, a dispersible polyolefin, a polymer latex and mixtures thereof, pigments and mixtures thereof, preferably said composition comprises an organic acid, preferably citric acid and/or lactic acid, hydrogenated castor oil, ethoxylated polyethleneimines, preferably PEI 600 EO 20 and/or PEI 600, an enzyme, preferably a cold water amylase, cold water protease and/or xylogluconase.

7.2 Antiperspirant Compositions

Antiperspirant compositions can be formulated in many forms. For example, an antiperspirant composition can be, without limitation, a roll on product, a body spray, a stick including soft solid sticks and invisible solids, or an aerosol. Each of the antiperspirant compositions described below can include fragrance materials as described herein, and can optionally further include additional fragrance materials, for example, to impart a more pleasing smell and/or to reduce, eliminate, or mask malodor, such as through antimicrobial or odor neutralizing effects.

One suitable embodiment of an antiperspirant is a roll-on antiperspirant composition, which can comprise, for example, water, emollient, solubilizer, deodorant actives, antioxidants, preservatives, or combinations thereof. A clear gel antiperspirant composition can comprise, for example, water, emollient, solubilizer, deodorant actives, antioxidants, preservatives, ethanol, or combinations thereof. Suitable deodorant actives for roll-on and clear gel antiperspirants can include any topical material that is known or otherwise effective in preventing or eliminating malodor associated with perspiration. Suitable deodorant actives can be selected from the group consisting of antimicrobial agents (e.g., bacteriocides, fungicides), malodor-absorbing material, and combinations thereof.

Another suitable embodiment of an antiperspirant is a body spray, which can contain, for example, a carrier, fragrance, a deodorant active, odor entrappers, propellant (e.g., compressed air, nitrogen, inert gases, carbon dioxide, etc.), or combinations thereof. The body spray compositions can be applied as a liquid.

Yet another suitable embodiment of an antiperspirant is an invisible solid antiperspirant composition, which can contain a primary structurant to help provide the antiperspirant with the desired viscosity, rheology, texture and/or product hardness, or to otherwise help suspend any dispersed solids or liquids within the composition or which otherwise provide structure to the final product form, an antiperspirant active, a fragrance, and additional chassis ingredients (e.g., additional structurants, solvents, non-volatile organic fluids, clay mineral powders, emulsifiers, distributing agents, preservatives, etc.). The antiperspirant composition can further comprise other optional ingredient(s).

Still another suitable embodiment of an antiperspirant is a soft solid antiperspirant, which can comprise volatile silicone, antiperspirant active, gellant, residue masking material, or combinations thereof. Soft solids generally have a hardness value after dispensing less than invisible solids. A soft solid can include a gellant material comprising fatty alcohols having from about 20 to about 60 carbon atoms, or combinations thereof, at concentrations ranging from about 0.1% to about 8% by weight of the composition. The gellant material, when combined with the volatile silicone solvent, provides the composition with a physically stable structure within which the particulate antiperspirant materials are dispersed, and maintained as such over an extended period of time. The soft solid compositions can further comprise one, or more, other materials which modify the physical characteristics of the compositions or serve as additional "active" components when deposited on the skin. Many such materials are known in the antiperspirant art and can be used in the antiperspirant compositions herein, provided that such optional materials are compatible with the essential materials described herein, or do not otherwise unduly impair product performance. Non limiting examples of materials can include active components such as bacteriostats and fungiostats, and "non-active" components such as colorants, fragrances, cosmetic powders, emulsifiers, chelants, distributing agents, preservatives, and wash-off aids.

An aerosol composition can comprise antiperspirant actives, a concentrate (e.g., alcohols, an oil or mixture of two or more oils, etc.), residue masking agents, a propellant, or a combination thereof.

7.3 Personal Care Compositions

Personal care compositions can include, but are not limited to, structurants (e.g., raw starch, such as corn, rice, potato, wheat and the like, carrageenan, xanthan gum, etc.), humectants (e.g., polyhydric alcohols, glycerin, etc.), fatty acids, inorganic salts (e.g., magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate, etc.), and antimicrobial agents (e.g., carbanilides, triclocarban, triclosan, a halogenated diphenylether, hexachlorophene, 3,4,5-tribromosalicylanilide, and salts of 2-pyridinethiol-1-oxide, salicylic acid, etc.), or other actives (such as by non-limiting example, anti-dandruff actives). Personal care compositions can take on numerous forms. Suitable personal care compostions include both rinse-off and solid form types.

Exemplary liquid rinse-off personal care compositions can include an aqueous carrier, such as water, which can be present at a level of from about 5% to about 95%, or from about 60% to about 85%. Non-aqueous carrier materials can also be employed. Such rinse-off personal care compositions can include one or more detersive surfactants. A representative, non-limiting, list of surfactants includes ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, be sodium 3-dodecyl-aminopropionate, sodium 3-dodecylaminopropane sulfonate, sodium lauroamphoacetate, sodium cocoamphoactetate, disodium lauroamphoacetate disodium cocodiamphoacetate, and cocoamidopropyl betaine.

Rinse-off personal care compositions can also include a benefit agent. Non-limiting examples of suitable benefit agents can include petrolatum, glyceryl monooleate, castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, isopropyl palmitate, isopropyl myristate, cetyl riconoleate, stearyl riconoleate, hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, decaglyceryl distearate, decaglyceryl diisostearate, decaglyceryl monomyriate, decaglyceryl monolaurate, hexaglyceryl monooleate, and mixtures thereof.

Solid (i.e., non-flowing) personal care compositions can take many forms like powder, pellets, bars, etc, and can comprise convention soap, synthetic surfactants, or a mix of soap and synthetic surfactant.

7.4 Air Care Compositions

The fragrance compounds, accords, and compositions disclosed herein are suitable for use in air care compositions for use in air care devices. The term "air care device" includes any suitable surface that allows for at least some evaporation of volatile materials in any suitable size, shape, form, or configuration can be used. Air care devices can be made from any suitable material providing for the evaporation of volatile materials, including without limitation: natural materials, man-made materials, fibrous materials, non-fibrous materials, porous materials, non-porous materials, and combinations thereof. One non-limiting example is a candle. Other examples of air care devices include aerosol, air freshener, liquid electric air freshener, fragrance diffuser, gel air freshener, plug-in air freshener, plug-in oil, and wax melt.

Air care devices (such as, wicking devices) are known for dispensing volatile liquids into the atmosphere, such as fragrance, deodorant, disinfectant or insecticide active agent. A typical air care device utilizes a combination of a wick and emanating region to dispense a volatile liquid from a liquid fluid reservoir. Air care devices are described in U.S. Pat. Nos. 1,994,932; 2,597,195; 2,802,695; 2,804,291; 2,847,976. Ideally, the air care device should require little or no maintenance and should perform in a manner that allows the volatile material to be dispensed at a steady and controlled rate into the designated area while maintaining its emission integrity over the life span of the device.

In certain embodiments, the air care composition can be incorporated into air fresheners. The air fresheners can be one or more sprays, plug in products, gel-type air fresheners, membrane-type air fresheners, nebulizers, diffusers, and potpourris.

In one suitable embodiment the air care composition described herein is for use in an electrical liquid air freshener device. The term "electrical liquid air freshener device" or "liquid electrical air freshener" refers to device or system that includes an electrical or battery operated source of energy which includes heated liquid wick delivery systems, piezoelectrical spraying systems, electrospray devices or Venturi devices. Commercial examples of electrical liquid air freshener devices include, but are not limited to, Glade PlugIns® Scented oil, sold by SC Johnson & Sons; Air Wick Scented Oils, and Air Wick X-Press® Scented Oils, sold by Reckitt Benckiser; Febreze Noticeables sold by Proctor & Gamble Co., Electric Home Air Fresheners, sold by the Yankee Candle Co.; and Renuzit Scented Oils, sold by Henkel AG.

In certain embodiments, candles can be one or more paraffin wax candles, beeswax candles, soy-based candles, tallow candles, and gel candles. A candle can have a candle wick centrally positioned in the body of the candle. The candle can emanate an air care composition and achieve continuous delivery of a fragrance compound, accord, or composition.

In another suitable embodiment, the air care composition is an aerosol for spraying the air in a room or other enclosed area. Such aerosol compositions can contain alcoholic or aqueous preparations of fragrance compositions, a propellant, surfactants, emulsifiers, and preservatives.

EXAMPLES

The presently disclosed subject matter will be better understood by reference to the following Examples, which are provided as exemplary of the disclosure, and not by way of limitation.

Example 1

Active Compounds Effective Against Stressors

Example 1 provides the results of seventeen compounds that demonstrated a change in salivary alpha-amylase levels, salivary cortisol levels, or both, in test panelists. Dipropylene glycol (DPG) was used as the solvent and control.

Stress was induced in each panelist using a timed mathematical and word test, which was administered to panelists in a small group competition setting to induce stress in each of the panelists. At set time intervals during the test, each panelist was exposed to either a single fragrance compound or to a DPG control.

Saliva was collected for each panelist before and immediately after the stress test. Saliva samples were assayed for salivary alpha-amylase activity and salivary cortisol levels using a commercially available assay kit (e.g., Salimetrics).

Table 1-A summarizes the percent change (i.e., before stress versus after stress) in the salivary alpha-amylase levels of panelists exposed to fragrance compounds of the present disclosure during the stress test. In addition, the table illustrates the statistical significance of the change in alpha-amylase levels (i.e., p-value or probability value, P) of each of the fragrance compounds as compared to DPG, representing the change in the control (i.e., just DPG without a fragrance compound before stress and after stress).

TABLE 1-A

| Tested Active Compound | % Change in Alpha-amylase (i.e., before versus after stress) |
|---|---|
| Ambroxide | −12.2% |
|  | P = 0.0129 vs. DPG |
| Bornyl Acetate, L | 27.1% |
|  | P = 0.4485 vs. DPG |
| Camphor | −11.6% |
|  | P = 0.0186 vs. DPG |
| Citral | 7.5% |
|  | P = 0.0833 vs. DPG |
| Citronellal | 4.9% |
|  | P = 0.1007 vs. DPG |
| Citronellol | 1.2% |
|  | P = 0.1013 vs. DPG |
| 3-(4-isopropylphenyl)-2-methylpropanal | 4.8% |
|  | P = 0.0743 vs. DPG |
| 2,4-di(tert-butyl)-cyclohexan-1-one | 10.9% |
|  | P = 0.134 vs DPG |
| Dihyrdomyrcene | 23.6% |
|  | P = 0.447 vs. DPG |
| Dihydromyrcenyl Acetate | −3.9% |
|  | P = 0.0394 vs. DPG |
| Eucalyptol | −11.1% |
|  | P = 0.0238 vs. DPG |
| Myrcenyl Acetate | 15.8% |
|  | P = 0.175 vs. DPG |
| 1-(1,2,3,4,5,6,7,8-octahydro-2,3,8,8,-tetramethyl-2-naphthyl)ethan-1-one | −2.5% |
|  | P = 0.0591 vs. DPG |
| 2,5,5-trimethyl-1,3,4,4a,6,7-hexahydronaphthalen-2-ol | 5.1% |
|  | P = 0.0888 vs. DPG |
| (1,7,7-trimethylbicyclo[2.2.1]hept-2-yl)-cyclohexanol | 3.8% |
|  | P = 0.0807 vs. DPG |
| 2-tert-butylcyclohexyl acetate | −4.3% |
|  | P = 0.033 vs. DPG |
| 1-cyclooct-4-enyl methyl carbonate | 15.2% |
|  | P = 0.1935 vs. DPG |
| DPG (control) | 51.9% |

Table 1-B summarizes the percent change (i.e., before stress versus after stress) in the salivary cortisol levels of panelists exposed to fragrance compounds of the present disclosure during the stress test. In addition, the table illustrates the statistical significance of the change in salivary cortisol levels (i.e., p-value or probability value, P) of each of the fragrance compounds as compared to DPG, representing the change in the control (i.e., just DPG without a fragrance compound before stress and after stress).

TABLE 1-B

| Tested Active Compound | % Change in Cortisol (i.e., before versus after stress) |
|---|---|
| Ambroxide | 1.1% |
|  | P = 0.4527 vs. DPG |
| Bornyl Acetate, L | −13.0% |
|  | P = 0.0751 vs. DPG |
| Camphor | −2.2% |
|  | P = 0.6142 vs. DPG |
| Citral | −2.8% |
|  | P = 0.3493 vs. DPG |
| Citronellal | 16.8% |
|  | P = 0.6727 vs. DPG |
| Citronellol | 3.4% |
|  | P = 0.5416 vs. DPG |
| 3-(4-isopropylphenyl)-2-methylpropanal | 17.73% |
|  | P = 0.6202 vs. DPG |
| 2,4-di(tert-butyl)-cyclohexan-1-one | 8.3% |
|  | P = 0.7818 vs. DPG |
| Dihyrdomyrcene | −8.1% |
|  | P = 0.1302 vs. DPG |

TABLE 1-B-continued

| Tested Active Compound | % Change in Cortisol (i.e., before versus after stress) |
|---|---|
| Dihydromyrcenyl Acetate | −13.3% |
|  | P = 0.1191 vs. DPG |
| Eucalyptol | −12.87% |
|  | P = 0.1201 vs. DPG |
| Myrcenyl Acetate | −6.9% |
|  | P = 0.202 vs. DPG |
| 1-(1,2,3,4,5,6,7,8-octahydro-2,3,8,8,-tetramethyl-2-naphthyl)ethan-1-one | −11.9% |
|  | P = 0.1051 vs. DPG |
| 2,5,5-trimethyl-1,3,4,4a,6,7-hexahydronaphthalen-2-ol | 30.0% |
|  | P = 0.554 vs. DPG |
| (1,7,7-trimethylbicyclo[2.2.1]hept-2-yl)-cyclohexanol | 1.0% |
|  | P = 0.4997 vs. DPG |
| 2-tert-butylcyclohexyl acetate | −14.2% |
|  | P = 0.1428 vs. DPG |
| 1-cyclooct-4-enyl methyl carbonate | 3.5% |
|  | P = 0.5854 vs. DPG |
| DPG (control) | 10.8% |

As shown in Table 1-A and Table 1-B, results of this study demonstrated that exposure to the fragrance compounds results in a decrease in salivary alpha-amylase and/or salivary cortisol levels as compared to the DPG control. Specifically, each of the fragrance compounds tested limited the increase in salivary alpha-amylase levels for the exposed panelists as compared to the control. In the presence of all but three tested fragrance compounds, the levels of salivary cortisol were limited to the exposed panelists as compared to the control.

Example 2

Stress Inhibiting Compositions

This Example provides examples of stress inhibiting accord compositions. Tables 2 through 8 provide components by weight percent of specific stress mixtures, Stress Mix A through Stress Mix G respectively, based on the active compounds of Example 1.

TABLE 2

| Stress Mix A | Weight % |
|---|---|
| Citrus materials | 60 |
| Woody materials | 40 |
| Total | 100 |

TABLE 3

| Stress Mix B | Weight % |
|---|---|
| Musk/woody materials | 4 |
| Citrus materials | 30 |
| Floral materials | 10 |
| Woody materials | 40 |
| Fruity materials | 16 |
| Total | 100 |

TABLE 4

| Stress Mix C | Weight % |
| --- | --- |
| Musk materials | 4 |
| Floral materials | 10 |
| Citrus materials | 10 |
| Woody materials | 60 |
| Fruity materials | 16 |
| Total | 100 |

TABLE 5

| Stress Mix D | Weight % |
| --- | --- |
| Woody materials | 40 |
| Piney materials | 20 |
| Citrus materials | 10 |
| Fruity materials | 30 |
| Total | 100 |

TABLE 6

| Stress Mix E | Weight % |
| --- | --- |
| Musk materials | 4 |
| Piney materials | 10 |
| Woody materials | 50 |
| Herbal materials | 20 |
| Fruity materials | 16 |
| Total | 100 |

TABLE 7

| Stress Mix F | Weight % |
| --- | --- |
| Woody materials | 40 |
| Citrus materials | 20 |
| Fruity materials | 40 |
| Total | 100 |

TABLE 8

| Stress Mix G | Weight % |
| --- | --- |
| Musk materials | 8 |
| Woody materials | 50 |
| Fruity materials | 40 |
| Green materials | 2 |
| Total | 100 |

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

Patents, patent applications publications product descriptions, and protocols are cited throughout this application the disclosures of which are incorporated herein by reference in their entireties for all purposes.

What is claimed is:

1. A method of reducing or inhibiting a stress response in a subject in need thereof comprising: administering a fragrance composition comprising:
   (i) (1,7,7-Trimethylbicyclo[2.2.1]hept-2-yl)-cyclohexanol;
   (ii) at least one fragrance compound selected from the group consisting of myrcenyl acetate and ambroxide; and
   (iii) at least one fragrance compound selected from the group consisting of bornyl acetate L, 3-(4-Isopropylphenyl)-2-methylpropanal, 2,4-Di(tert-butyl)-cyclohexan-1-one, Dihyrdomyrcene, Dihydromyrcenyl acetate, eucalyptol, 1-(1,2,3,4,5,6,7,8-Octahydro-2,3,8,8,-tetramethyl-2-naphthyl)ethan-1-one, 2,5,5-Trimethyl-1,3,4,4a,6,7-hexahydronaphthalen-2-ol, 2-tert-Butylcyclohexyl acetate, and 1-Cyclooct-4-enyl methyl carbonate to the subject in an amount effective to reduce or inhibit a response to stress stimuli, wherein the stress response is measured by a change in salivary alpha-amylase levels, salivary cortisol levels, or both.

2. The method of claim 1, wherein the composition is administered before, during, or after exposure to the stress stimuli.

3. The method of claim 1, wherein the composition comprises from about 0.001 wt % to about 100 wt % fragrance compounds.

4. The method of claim 1, wherein the composition comprises from about 0.001 wt % to about 10 wt % fragrance compounds.

5. The method of claim 1, wherein the composition comprises from about 1 wt % to about 80 wt % eucalyptol.

6. The method of claim 1, wherein the composition comprises from about 1 wt % to about 31 wt % bornyl acetate L.

7. The method of claim 1, wherein the composition comprises ambroxide, 3-(4-isopropylphenyl)-2-methylpropanal, myrcenyl acetate, (1,7,7-Trimethylbicyclo[2.2.1]hept-2-yl)-cyclohexanol, and 2-tert-butylcyclohexyl acetate.

8. The method of claim 1, wherein the composition comprises bornyl acetate L, alpha terpineol, myrcenyl acetate, 2-(2-(4-methyl-3-cyclohexen-1-y-propyl)cyclopentanone, (1,7,7-Trimethylbicyclo[2.2.1]hept-2-yl)-cyclohexanol, and 2-tert-butylcyclohexyl acetate.

9. The method of claim 1, wherein the composition comprises ambroxide, alpha terpineol, (1,7,7-Trimethylbicyclo[2.2.1]hept-2-yl)-cyclohexanol, terpinyl acetate, and 2-tert-butylcyclohexyl acetate.

10. The method of claim 1, wherein the composition comprises bornyl acetate, myrcenyl acetate, 2-(2-(4-methyl-3-cyclohexen-1-yl)propyl)cyclopentanone, (1,7,7-Trimethylbicyclo[2.2.1]hept-2-yl)-cyclohexanol, and 2-tert-butylcyclohexyl acetate.

11. The method of claim 1, wherein the composition comprises ambroxide, (1,7,7-Trimethylbicyclo[2.2.1]hept-2-yl)-cyclohexanol, 2-tert-butylcyclohexyl acetate, and 1-cyclooct-4-enyl methyl carbonate.

* * * * *